US00PP09481P

United States Patent [19]

Challet

[11] Patent Number: Plant 9,481

[45] Date of Patent: Mar. 19, 1996

[54] CHRYSANTHEMUM PLANT NAMED 'CHAREMI'

[75] Inventor: Jean-Pierre Challet, Lafayette, Calif.

[73] Assignee: Selection New Plant Sarl, Le Cannet des Maures, France

[21] Appl. No.: 274,002

[22] Filed: Jul. 12, 1994

[51] Int. Cl.[6] ..... A01H 5/00

[52] U.S. Cl. ..... Plt./80

[58] Field of Search ..... Plt./76, 80, 81

[56] References Cited

U.S. PATENT DOCUMENTS

| | | | |
|---|---|---|---|
| P.P. 3,221 | 6/1972 | Jessel, Jr. et al. | Plt./80 |
| P.P. 3,289 | 1/1973 | Gentile et al. | Plt./80 |
| P.P. 3,311 | 2/1973 | Jessel, Jr. et al. | Plt./80 |
| P.P. 6,937 | 7/1989 | Sanford | Plt./80 |

*Primary Examiner*—Howard J. Locker
*Attorney, Agent, or Firm*—Burns, Doane, Swecker & Mathis

[57] ABSTRACT

A new and distinct Chrysanthemum cultivar named 'Charemi' is provided. The new cultivar was the result of a controlled breeding program. Attractive very large double incurved light pink blossoms of the pompon type are formed generally in the shape of a round ball. The blossoms keep their form for weeks without showing an open center. The response period of the flowers is approximately eight weeks. Recurrent profuse flower production throughout the year is possible. The plant possesses strong stems, forms large deep green leaves, and commonly assumes a height of only approximately 30 to 35 cm. The new cultivar is particularly suited for use in the production of a decorative pot Chrysanthemum and can be grown single-stem, disbudded, or center-budded. No growth regulator is required to achieve the short plant height.

3 Drawing Sheets

SUMMARY OF THE INVENTION

The present invention comprises a new and distinct cultivar of Chrysanthemum, botanically known as *Dendranthema grandiflorum*, and hereinafter is referred to by the cultivar name 'Charemi'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during October 1987 at Nuaille, Trementines, France. The female parent (i.e., the seed parent) was an unnamed plant designated 84-124-2 (non-patented in the United State) having a large pink pompon flower that was bred during 1978 which lacked an ability to flower regularly, and the male parent (i.e., the pollen parent) was unnamed plant designated 78-48-4 (non-patented in the United States) having a large double soft pink pompon flower that was bred during 1984 and had a tendency to fade quickly under high intensity light conditions. The parentage of the new cultivar can be summarized as follows:

84-124-2×78-48-4.

The seeds resulting from the above pollination were sown and many small plantlets were obtained which were physically and biologically different from each other. Selective study resulted in the identification of a single plant of the new variety.

It was found that the new cultivar of the present invention:

(a) exhibits attractive double incurved light pink pompon blossoms generally in the form of a large ball,
(b) exhibits a flower response period of approximately eight weeks,
(c) forms attractive dark green foliage,
(d) achieves a short plant height, and
(e) is particularly suited for pot mum production on a recurrent basis throughout the year.

The new cultivar is intended primarily as a decorative pot Chrysanthemum for growing indoors. However, it also can be grown for cut flower production in those instances where stems of approximately 30 cm. are acceptable. Also, the new cultivar can be grown outdoors at temperatures above freezing.

In the absence of debudding commonly 6 to 7 blossoms form per stem. The new cultivar can be grown single-stem, with disbudding, or center budded. An increased number of branches readily can be induced by pinching. The pinching of a cutting commonly produces 3 to 4 stems. No growth regulator is required to produce the short plant height.

The new cultivar can be considered to be an October-flowering greenhouse variety with the natural flowering season commonly occurring in weeks 41 and 42 of the year. Attractive blossoms can be produced on a recurrent basis throughout the year with the indicated eight week response period. The blossoms are long lasting and commonly can be maintained on the plant for two to three weeks, and for three to four weeks when cut and placed in a vase.

Asexual reproduction of the new culivar by cuttings initially taken during 1988, as performed in Nuaille, Trementines, France, in a controlled environment has demonstrated that the characteristics of the new cultivar as herein described are firmly fixed and are retained through successive generations of asexual propagation.

'Charemi' has not been observed under all possible environmental conditions to date. Accordingly, it is possible that the phenotype may vary somewhat with variations in the environment, such as temperature, light, day length, contact with pesticides and/or subjection to growth retardant treatments.

When the new culivar of the present invention is compared to the 'Peacock' cultivar (non-patented in the United States), the 'Charemi' cultivar is found to exhibit a faster response period of approximately 8 weeks vs. 10 weeks, a lighter blossom coloration, and a shorter plant height.

The new cultivar is being marketed under the CHIME trademark.

BRIEF DESCRIPTION OF THE PHOTOGRAPHS

The accompanying photographs were prepared during June, 1994, and show as nearly true as it is reasonably possible to make the same in color illustrations of this character, typical plants and plant parts of the new cultivar of the present invention. The plants were 11 weeks of age and were grown at Nuaille, Trementines, France, under standard greenhouse conditions which approximate those commonly utilized for the production of decorative pot mums. The plant had been disbudded in order to encourage the formation of one large bloom per stem. Any labels shown in the photographs are 2.5 cm. in width and can be used for size comparisons.

DETAILED DESCRIPTION

Figure 1:
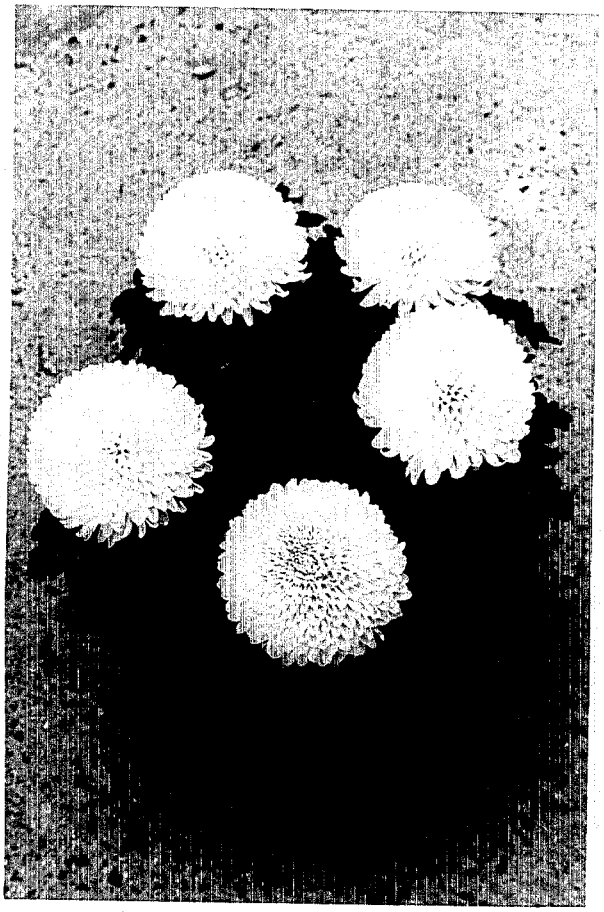
FIG. 1 illustrates typical specimens of the overall plant wherein five cuttings were placed in a 20 cm. pot. The large pale pink incurved flowers generally in the form of large round balls, as well as the foliage, are apparent.
Figure 2:
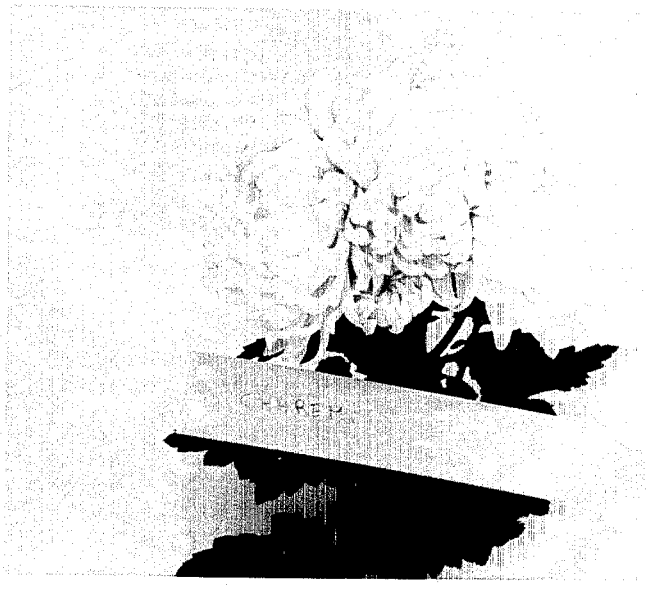
FIG. 2 illustrates a side view of a typical open flower.
Figure 3:
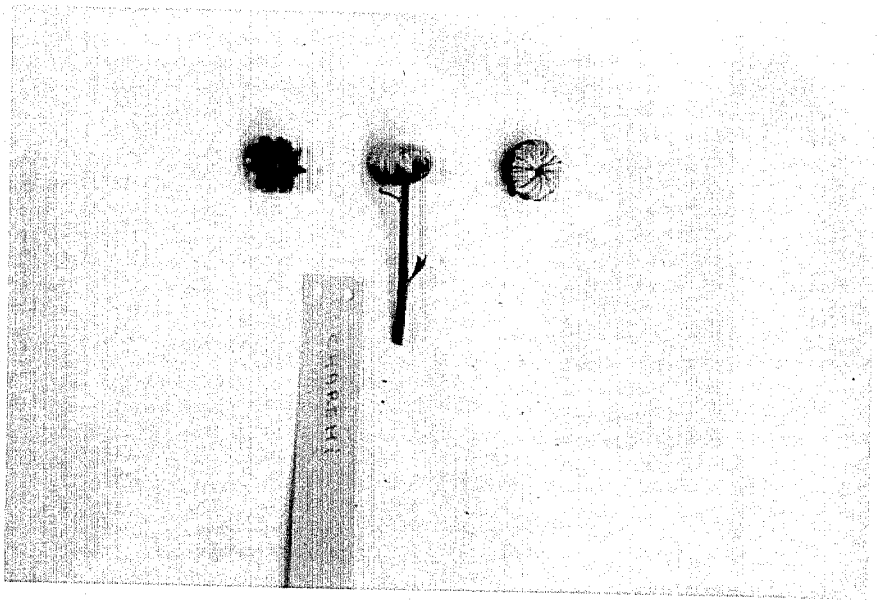
FIG. 3 illustrates from left to right under, side, and top views of unopened buds.
Figure 4:
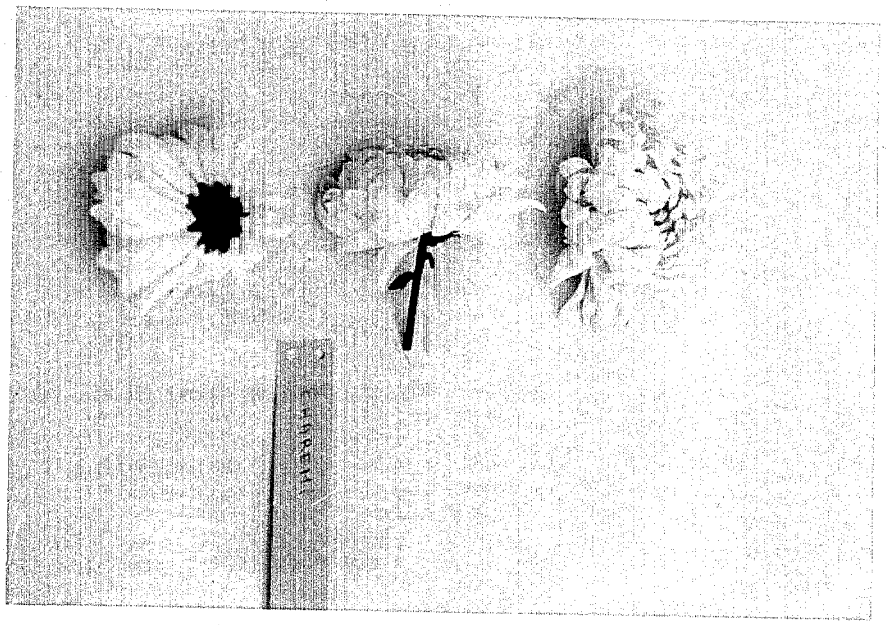
FIG. 4 illustrates under, side, and top views of the flowers in the course of opening.
Figure 5:
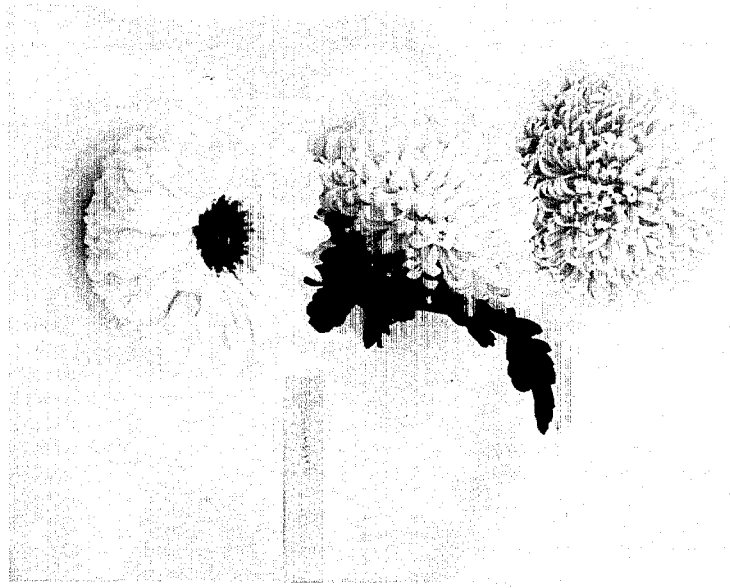
FIG. 5 illustrates under, side, and top views of fully open flowers.
Figure 6:
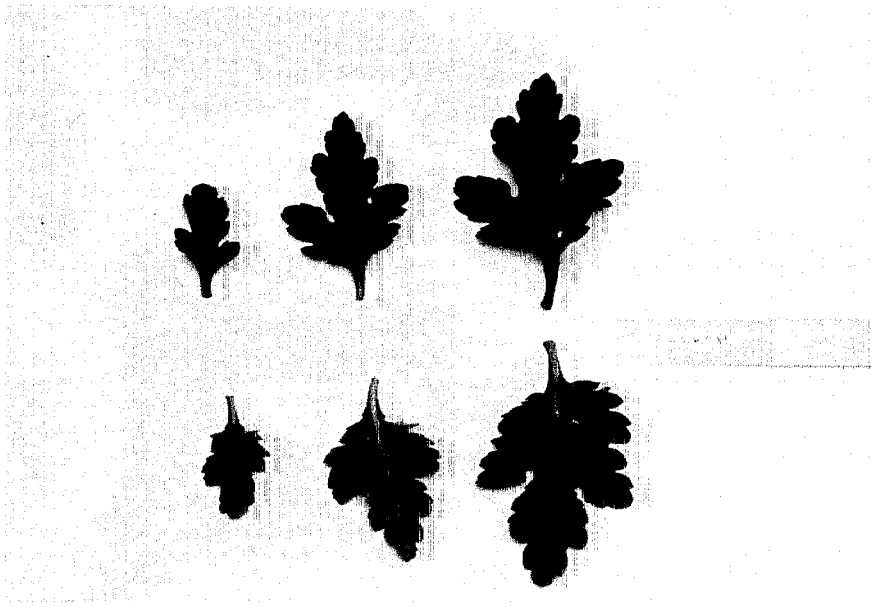
FIG. 6 illustrates at the top row the upper surfaces of typical leaves of various sizes and at the bottom row the under surfaces of typical leaves of various sizes.

The chart used in the identification of color described hereafter is the R.H.S. Colour Chart of The Royal Horticultural Society, London, England. In some instances more common color terms are provided and are to be accorded their usual dictionary significance. The plants described were 11 weeks of age and were grown at Nuaille, Trementines, France, under standard greenhouse conditions where approximate those commonly utilized for the production of decorative pot mums.

Classification:

*Botanical.*—*Dendranthema grandiflorum*, cv. 'Charemi'.

*Commercial.*—Decorative pot mum.

INFLORESCENCE

A. Capitulum:

*Form.*—Large, double, incurved. The outside rows of petals may change to a semi-incurved configuration upon maturity.

*Type.*—Pompon.

*Diameter across face.*—Approximately 12 to 13 cm. on average when fully expanded.

B. Corolla of ray and disc florets:

*Color of bud.*—Commonly lighter than Greyed-Purple Group 186D.

*Disc florets.*—Tubular, yellow in coloration, few in number, very difficult to observe, and tend to be scattered among the ray florets with a small cluster at the apex of the receptable that is visible only when the ray florets are removed.

*General tonality.*—At the beginning of flowering the blossoms appear to be bicolored with soft pink on the outer rows of ray floret and deeper pin on the inner rows of ray florets. The initial bicoloration can be attributed to differences in maturity between the inner rows of ray florets and the outer rows of ray florets. As the blossoms mature, the inner rows of ray florets tend to fade to a soft pink, and finally all of the ray florets become a soft pink to nearly white. The rate of fade is influenced by the temperature and light intensity that is experienced which tends to induce a change in color pigmentation.

*Color ray florets.*—Lighter than Red-Purple Group 69B on the outer side, and Red-Purple Group 69B on the inner side.

*Configuration ray florets.*—Concave in cross section, textured, and possess pointed tips.

C. Reproductive organs:

*Androecium.*—Generally present with disc florets and absent in ray florets.

*Gynoecium.*—Generally present with most disc florets and with most ray florets.

*Pollen.*—Formed in a slight quantity and golden-yellow in coloration.

*Fragrance.*—Typical of Chrysanthemum.

PLANT

A. General Appearance:

*Height.*—Short, and approximately 30 to 35 cm. in height on average.

B. Foliage:

*Color (upper surface).*—Dark green, Green Group 137A.

*Color (lower surface).*—Lighter green, approaches Green Group 138A.

*Long day leaf count.*—Approximately 32 to 35 leaves per typical stem in a long day crop before the bud occurs.

*Configuration.*—Lobed (as illustrated).

*Texture.*—Fleshy.

*Internode length.*—Very short.

*Stem.*—Thin, strong, angular in cross section, nearest to Yellow-Green Group 144A in coloration, and commonly with anthocyanin coloration at the base.

I claim:

1. A new and distinct cultivar of Chrysanthemum plant named 'Charemi', substantially as herein shown and described, which (a) exhibits attractive double incurved light pink pompon blossoms generally in the form of a large ball, (b) exhibits a flower response period of approximately eight weeks, (c) forms attractive dark green foliage, (d) achieves a short plant height, and (e) is particularly suited for pot mum production on a recurrent basis throughout the year.

* * * * *